United States Patent
Winter et al.

[11] Patent Number: 6,150,481
[45] Date of Patent: *Nov. 21, 2000

[54] PROCESS FOR THE PREPARATION OF POLYOLEFINS

[75] Inventors: Andreas Winter, Glashütten; Walter Spaleck, Liederbach; Bernd Bachmann, Eppstein, all of Germany

[73] Assignee: Targor GmbH, Germany

[*] Notice: This patent is subject to a terminal disclaimer.

[21] Appl. No.: 08/920,141

[22] Filed: Aug. 26, 1997

Related U.S. Application Data

[63] Continuation of application No. 08/667,477, Jun. 24, 1996, Pat. No. 5,696,045, which is a continuation of application No. 08/312,718, Sep. 27, 1994, abandoned.

[30] Foreign Application Priority Data

Sep. 29, 1993 [DE] Germany .............................. 43 33 128

[51] Int. Cl.[7] ...................................................... C08F 2/00
[52] U.S. Cl. ........................... 526/118; 526/119; 526/160; 526/348; 526/351; 502/113; 502/117
[58] Field of Search .................................... 526/118, 119, 526/160, 351, 348; 502/113, 117

[56] References Cited

U.S. PATENT DOCUMENTS

| | | | |
|---|---|---|---|
| 4,530,914 | 7/1985 | Ewen et al. | |
| 4,849,487 | 7/1989 | Kaminsky et al. | |
| 4,892,851 | 1/1990 | Ewen et al. | 502/104 |
| 4,935,474 | 6/1990 | Ewen et al. | 526/114 |
| 4,939,217 | 7/1990 | Stricklen | |
| 4,975,403 | 12/1990 | Ewen | 502/113 |
| 5,132,381 | 7/1992 | Winter et al. | |
| 5,243,001 | 9/1993 | Winter et al. | 526/127 |
| 5,278,264 | 1/1994 | Spaleck et al. | 526/127 |
| 5,296,434 | 3/1994 | Karl et al. | 502/117 |
| 5,304,614 | 4/1994 | Winter et al. | 526/127 |
| 5,328,696 | 7/1994 | Winter et al. | |
| 5,328,969 | 7/1994 | Winter et al. | 526/127 |
| 5,350,817 | 9/1994 | Winter et al. | 526/119 |

FOREIGN PATENT DOCUMENTS

| | | |
|---|---|---|
| 39056 | 2/1990 | Australia . |
| 651915 | 6/1993 | Australia . |
| 2017190 | 11/1990 | Canada . |
| 2069602 | 11/1992 | Canada . |
| 1317411 | 5/1993 | Canada . |
| 2099214 | 12/1993 | Canada . |
| 0 128 045 | 12/1984 | European Pat. Off. . |
| 0 302 424 | 2/1989 | European Pat. Off. . |
| 0 310 734 | 4/1989 | European Pat. Off. . |
| 0 355 439 | 2/1990 | European Pat. Off. . |
| 0 387 691 | 9/1990 | European Pat. Off. . |
| 0 516 018 | 12/1992 | European Pat. Off. . |
| 36 40 924 | 6/1988 | Germany . |
| 92/15619 | 9/1992 | WIPO . |

OTHER PUBLICATIONS

Giannetti et al, "Homogeneous Ziegler–Natta Catalysis II. Ethylene Polymerization by IVB Transition Metal Complexes/Methyl Aluminoxane Catalyst Systems", J. Pol. Sci., Pol. Chem. Ed. 23 (1985) pp. 2117–2134.

*Primary Examiner*—David W. Wu
*Assistant Examiner*—Ling-Siu Choi
*Attorney, Agent, or Firm*—Connolly Bove Lodge & Hutz LLP

[57] ABSTRACT

Polyolefins with a molecular weight distribution $M_w/M_n \geq 3.0$, which may be monomodal, bimodal or multimodal, can be obtained by polymerization or copolymerization of olefins with a catalyst system consisting of an aluminoxane and a transition metal component (metallocene), in which the transition metal component consists of at least one zirconocene of the formula I and at least one zirconocene of the formula Ia

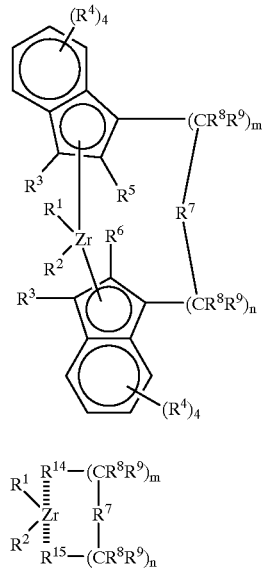

or alternatively of at least 2 zirconocenes of the formula I.

13 Claims, No Drawings

PROCESS FOR THE PREPARATION OF POLYOLEFINS

This application is a continuation of Ser. No. 08/667,477 filed Jun. 24, 1996 now U.S. Pat. No. 5,696,045, which in turn is a continuation of Ser. No. 08/312,718 filed Sep. 27, 1994 which is now abandoned.

The invention relates to a process for the preparation of polyolefins having a wide molecular weight distribution and high molecular weight.

It is known that metallocene catalysts together with aluminoxanes can polymerize olefins into polyolefins having a narrow molecular weight distribution ($M_w/M_n$ of 2–3) (J. Polym. Sci, Pol. Chem. Ed. 23 (1985) 2117; EP-A 302 424). Polyolefins of this type having a narrow molecular weight distribution are suitable, for example, for applications in precision injection moulding, general injection moulding and fibre production. For numerous applications such as thermoforming, extrusion, blow moulding and the production of polyolefin foams and films, wider or bimodal molecular weight distribution is required.

It was suggested that for polyethylene such products could be obtained by using two or more metallocene catalysts in polymerization (EP-A 128 045); the systems described are however achiral catalysts and in the polymerization of propene would yield atactic polypropylene. Atactic polypropylene is however unsuitable as an engineering polymer.

The preparation of stereo block polypropylene with $M_w/M_n$ of 13–15 is known from DE-OS 3 640 924. These catalyst systems are likewise unsuitable for forming polyolefins of high tacticity. Furthermore, the levels of metallocene activity and molecular weight of the polymer products achievable at the industrially relevant polymerization temperatures are too low. Moreover, the suggested catalysts yield only atactic polymer at such polymerization temperatures.

In EP-A 310 734, catalyst systems consisting of a mixture of a hafnocene and a zirconocene are suggested for the preparation of polypropylene. The products have wide to bimodal distribution with $M_w/M_n$ of 3.7 to 10.3.

According to EP-A 355 439, by using only one hafnocene catalyst at a specified polymerization temperature, polypropylene having a wide molecular weight distribution is obtained.

Syndiotactic polypropylene having a wide molecular weight distribution ($M_w/M_n$ up to 6.4) prepared by using a hafnocene is described in EP-A 387 691.

The disadvantages common to these processes are the excessive costs of the hafnium catalysts for industrial applications and their low polymerization activity, which makes thorough, cost-intensive cleaning of the prepared polymer necessary to remove catalyst residues (high residual ash content).

In EP-A-O 516 018, the use of two zirconocenes to prepare polymers having a wide molecular weight distribution is described. The metallocenes described there, however, have deficiencies in polymerization activity and in achievable molecular weight level at the industrially relevant polymerization temperatures of over 50° C.

Accordingly, the object was to find a catalyst system and a process by means of which polyolefins having a wide, bimodal or multimodal distribution could be prepared and which avoided the known disadvantages of state-of-the-art-technology.

In particular, the new process had to avoid the high residual ash content arising from low polymerization activity and enable the preparation of high-molecular-weight polymer moulding materials such as are required, for example, for production of compression moulded sheets, extruded sheets and pipes, and blow mouldings of all sizes. Preferred applications for such polymers with low flowability are, for example, blow moulded cases with integral hinges, skin packaging, sheet material for die punching, hot water tanks, wastewater and hot water pipes, pressure pipes, filter plates, heat exchangers, solid rods or automotive parts such as brake fluid reservoirs and radiator expansion tanks. In the films sector, these moulding materials are used for tear-resistant BOPP films.

Surprisingly, it was found that the disadvantages of state-of-the-art technology can be avoided by using a catalyst system consisting of at least two stereorigid zirconocenes, of which at least one has substituted indenyl ligands on the six-membered ring, and an aluminium compound as co-catalyst.

The invention thus relates to a process for the preparation of a polyolefin having a molecular weight distribution $M_w/M_n \geq 3.0$, which may be monomodal, bimodal or multimodal, by polymerization or copolymerization of an olefin of the formula $R^aCH=CHR^b$, in which $R^a$ and $R^b$ are identical or different and are a hydrogen atom or an alkyl radical with 1 to 14 C atoms, or $R^a$ and $R^b$ may form a ring system together with the atoms connecting them, at a temperature of 50–200° C., at a pressure of 0.5 to 100 bar, in solution, in suspension or in the gas phase, in the presence of a catalyst which consists of a transition metal component (metallocene) and an aluminoxane of the formula II

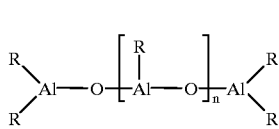

(II)

for the linear type and/or formula III

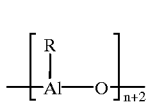

(III)

for the cyclic type, in which the radicals R in formulae II and III may be identical or different and are a $C_1$–$C_6$ alkyl group, a $C_1$–$C_6$ fluoroalkyl group, a $C_6$–$C_{18}$ aryl group, a $C_1$–$C_6$ fluoroaryl group or hydrogen and n is an integer from 0 to 50, or, instead of the aluminoxane, a mixture of an aluminoxane of the formula II and/or the formula III with an $AlR_3$ compound, characterized by the fact that at least one zirconocene of the formula I and at least one zirconocene of the formula Ia or alternatively at least 2 zirconocenes of the formula I are used as the transition metal component, (I)

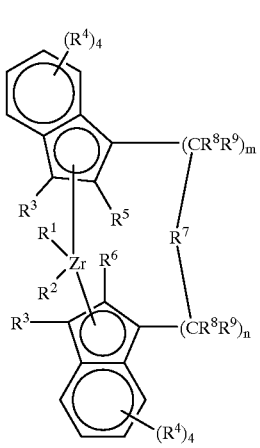

-continued

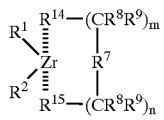
(Ia)

in which
- $R^1$ and $R^2$ are identical or different and are a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_7$–$C_{40}$ arylalkyl group, a $C_7$–$C_{40}$ alkylaryl group, a $C_8$–$C_{40}$ arylalkenyl group or a halogen atom,
- $R^3$ are hydrogen, a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group,
- $R^4$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, where at least one $R^4$ radicals per indenyl ring is different from hydrogen, or two or more $R^4$ radicals form a ring system with the atoms connecting them,
- $R^5$ and $R^6$ are identical or different and are a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group,
- $R^7$ is

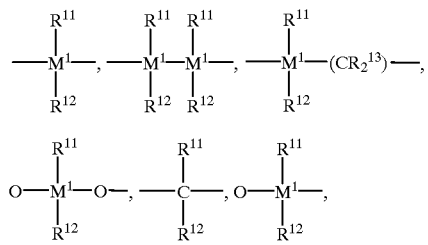

=$BR^{11}$, =$AlR^{11}$, —Ge—, —Sn—, —O—, —S—, =SO, =$SO_2$, =$NR^{11}$, =CO, =$PR^{11}$ or $P(O)R^{11}$, where $R^{11}$, $R^{12}$ and $R^{13}$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or $R^{11}$ and $R^{12}$ or $R^{11}$ and $R^{13}$ each form a ring with the atoms connecting them, $M^1$ is silicon, germanium or tin,

- $R^8$ and $R^9$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or $R^8$ and $R^9$ each form a ring with the atoms connecting them,
- $R^{14}$ and $R^{15}$ are identical or different and are a monocyclic or polycyclic hydrocarbon radical, which may form a sandwich structure with the zirconium atom and
- m and n are identical or different and are zero, 1 or 2, with m plus n being equal to zero, 1 or 2.

Alkyl denotes linear or branched alkyl. Halogen (halogenated) means fluorine, chlorine, bromine or iodine, preferably fluorine or chlorine.

$R^1$ and $R^2$ are identical or different and are a hydrogen atom, a $C_1$–$C_{10}$, preferably $C_1$–$C_3$, alkyl group, a $C_1$–$C_{10}$, preferably $C_1$–$C_3$, alkoxy group, a $C_6$–$C_{10}$, preferably $C_6$–$C_8$, aryl group, a $C_6$–$C_{10}$, preferably $C_6$–$C_8$, aryloxy group, a $C_2$–$C_{10}$, preferably $C_2$–$C_4$, alkenyl group, a $C_7$–$C_{40}$, preferably $C_7$–$C_{10}$, arylalkyl group, a $C_7$–$C_{40}$, preferably $C_7$–$C_{12}$, alkylaryl group, a $C_8$–$C_{40}$, preferably $C_8$–$C_{12}$, arylalkenyl group or a halogen atom, preferably chlorine.

$R^3$ is hydrogen, a halogen atom, preferably a fluorine, chlorine or bromine atom, a $C_1$–$C_{10}$, preferably $C_1$–$C_4$, alkyl group, which may be halogenated, a $C_6$–$C_{10}$, preferably $C_6$–$C_8$, aryl group, a $C_2$–$C_{10}$, preferably $C_2$–$C_4$, alkenyl group, a $C_7$–$C_{40}$, preferably $C_7$–$C_{10}$, arylalkyl group, a $C_7$–$C_{40}$, preferably $C_7$–$C_{12}$, alkylaryl group, a $C_8$–$C_{40}$, preferably $C_8$–$C_{12}$, arylalkenyl group, an —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$, preferably $C_1$–$C_3$, alkyl group or $C_6$–$C_{10}$, preferably $C_6$–$C_8$, aryl group, with $R^3$ as hydrogen being specially preferred.

The $R^4$ radicals are identical or different and are a hydrogen atom, a halogen atom, a $C_1$–$C_{20}$, preferably $C_1$–$C_{10}$, alkyl group, a $C_1$–$C_{20}$, preferably $C_1$–$C_{10}$, fluoroalkyl group, a $C_6$–$C_{30}$, preferably $C_6$–$C_{20}$, aryl group, a $C_6$–$C_{30}$, preferably $C_6$–$C_{20}$, fluoroaryl group, a $C_1$–$C_{20}$, preferably $C_1$–$C_{10}$, alkoxy group, a $C_2$–$C_{20}$, preferably $C_2$–$C_{10}$, alkenyl group, a $C_7$–$C_{40}$, preferably $C_7$–$C_{20}$, arylalkyl group, a $C_8$–$C_{40}$, preferably $C_8$–$C_{22}$, arylalkenyl group or a $C_7$–$C_{40}$, preferably $C_7$–$C_{22}$, alkylaryl group, an —$NR_2^{10}$, —$SR^{10}$, —$OSiR_3^{10}$, —$OR^{10}$, —$SiR_3^{10}$ or —$PR_2^{10}$ radical, in which $R^{10}$ is a halogen atom, preferably a chlorine atom, or a $C_1$–$C_{10}$, preferably $C_1$–$C_3$, alkyl group or $C_6$–$C_{10}$, preferably $C_6$–$C_8$, aryl group, where at least one $R^4$ radicals per indenyl ring is different from hydrogen, or two or more $R^4$ radicals form a ring system with the atoms connecting them, which is mono- or polycyclic.

$R^5$ and $R^6$ are identical or different and are a halogen atom, preferably a fluorine, chlorine or bromine atom, a $C_1$–$C_{10}$, preferably $C_1$–$C_4$, alkyl group, which may be halogenated, a $C_6$–$C_{10}$, preferably $C_6$–$C_8$, aryl group, a $C_2$–$C_{10}$, preferably $C_2$–$C_4$, alkenyl group, a $C_7$–$C_{40}$, preferably $C_7$–$C_{10}$, arylalkyl group, a $C_7$–$C_{40}$, preferably $C_7$–$C_{12}$, alkylaryl group, a $C_8$–$C_{40}$, preferably $C_8$–$C_{12}$, arylalkenyl group, an —$NR_2^{10}$, —$SR^{10}$, $OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$, preferably $C_1$–$C_3$, alkyl group or $C_6$–$C_{10}$, preferably $C_6$–$C_8$, aryl group.

$R^7$ is

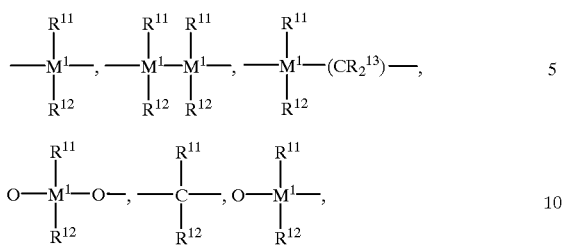

$=BR^{11}$, $=AlR^{11}$, —Ge—, —Sn—, —O—, —S—, $=SO$, $=SO_2$, $=NR^{11}$, $=CO$, $=PR^{11}$ or $P(O)R^{11}$, where $R^{11}$, $R^{12}$ and $R^{13}$ are identical or different and are a hydrogen atom, a halogen atom, a $C_1$–$C_{20}$, preferably $C_1$–$C_{10}$, alkyl group, a $C_1$–$C_{20}$, preferably $C_1$–$C_{10}$, fluoroalkyl group, a $C_6$–$C_{30}$, preferably $C_6$–$C_{20}$, aryl group, a $C_6$–$C_{30}$, preferably $C_6$–$C_{20}$, fluoroaryl group, a $C_1$–$C_{20}$, preferably $C_1$–$C_{10}$, alkoxy group, a $C_2$–$C_{20}$, preferably $C_2$–$C_{10}$, alkenyl group, a $C_7$–$C_{40}$, preferably $C_7$–$C_{20}$, arylalkyl group, a $C_8$–$C_{40}$, preferably $C_8$–$C_{22}$, arylalkenyl group or a $C_7$–$C_{40}$, preferably $C_7$–$C_{22}$, alkylaryl group, or $R^{11}$ and $R^{12}$ or $R^{11}$ and $R^{13}$ each form a ring with the atoms connecting them.

$M^1$ is silicon, germanium or tin, preferably silicon and germanium.

$R^7$ is preferably $=CR^{11}R^{12}$, $=SiR^{11}R^{12}$, $=GeR^{11}R^{12}$, —O—, —S—, $=SO$, $=PR^{11}$ or $=P(O)R^{11}$.

$R^8$ and $R^9$ are identical or different and are a hydrogen atom, a halogen atom, a $C_1$–$C_{20}$, preferably $C_1$–$C_{10}$, alkyl group, a $C_1$–$C_{20}$, preferably $C_1$–$C_{10}$, fluoroalkyl group, a $C_6$–$C_{30}$, preferably $C_6$–$C_{20}$, aryl group, a $C_6$–$C_{30}$, preferably $C_6$–$C_{20}$, fluoroaryl group, a $C_1$–$C_{20}$, preferably $C_1$–$C_{10}$, alkoxy group, a $C_2$–$C_{20}$, preferably $C_2$–$C_{10}$, alkenyl group, a $C_7$–$C_{40}$, preferably $C_7$–$C_{20}$, arylalkyl group, a $C_8$–$C_{40}$, preferably $C_8$–$C_{22}$, arylalkenyl group or a $C_7$–$C_{40}$, preferably $C_7$–$C_{22}$, alkylaryl group or $R^8$ and $R^9$ each form a ring with the atoms connecting them.

m and n are identical or different and are zero, 1 or 2, preferably zero or 1, with m plus n being equal to zero, 1 or 2, preferably zero or 1.

$R^{14}$ and $R^{15}$ are preferably fluorenyl, indenyl and cyclopentadienyl and these basic structures may carry additional substituents in the meaning of $R^4$. In the case of an indenyl basic structure, the six-membered ring may not however contain any substituents which are different from hydrogen if the five-membered ring in the 2 position (adjacent to the bridge —$(CR^8R^9)_m$—$R^7$—$(CR^8R^9)$—) carries a radical $R^5$ or $R^6$ which is different from hydrogen.

Thus the specially preferred metallocenes are those in which in formula I, $R^1$ and $R^2$ are identical or different and are methyl or chlorine, $R^3$ is hydrogen and $R^7$ is a radical

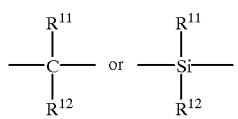

with n plus m being equal to zero or 1; in particular such compounds of formula I, in which the indenyl radicals are substituted in the 2,4-, 2,5-, 2,4,6-, 2,4,5-, 2,4,5,6-, and 2,5,6-positions, such as eg:

dimethylsilanediylbis(2-methyl-4-phenyl-1-indenyl)ZrCl$_2$ phenyl(methyl)silanediylbis(2-methyl-4-phenyl-1-indenyl)ZrCl$_2$ dimethylsilanediylbis(2-methyl-4-(1-naphthyl)-1-indenyl)ZrCl$_2$ dimethylsilanediylbis(2-methyl-4-(2-naphthyl)-1-indenyl)ZrCl$_2$ dimethylsilanediylbis(2-ethyl-4-(1-naphthyl)-1-indenyl)ZrCl$_2$ dimethylsilanediylbis(2-methyl-4,6-diisopropyl-1-indenyl)ZrCl$_2$ dimethylsilanediylbis(2,4,6-trimethyl-1-indenyl)ZrCl$_2$ phenyl(methyl)silanediylbis(2-methyl-4,6-diisopropyl-1-indenyl)ZrCl$_2$ phenyl(methyl)silanediylbis(2,4,6-trimethyl-1-indenyl)ZrCl$_2$ 1,2-ethanediylbis(2-methyl-4,6-diisopropyl-1-indenyl)ZrCl$_2$ 1,2-butanediylbis(2-methyl-4,6-diisopropyl-1-indenyl)ZrCl$_2$ dimethylsilanediylbis(2-methyl-4-ethyl-1-indenyl)ZrCl$_2$ dimethylsilanediylbis(2-methyl-4-isopropyl-1-indenyl)ZrCl$_2$ dimethylsilanediylbis(2-methyl-4-t-butyl-1-indenyl)ZrCl$_2$ phenyl(methyl)silanediyibis(2-methyl-4-isopropyl-1-indenyl)ZrCl$_2$ dimethylsilanediylbis(2-ethyl-4-methyl-1-indenyl)ZrCl$_2$ dimethylsilanediylbis(2,4-dimethyl-1-indenyl)ZrCl$_2$ dimethylsilanediylbis(2-methyl-4-ethyl-1-indenyl)ZrCl$_2$ dimethylsilanediylbis(2-methyl-α-acenaphth-1-indenyl)ZrCl$_2$ phenyl(methyl)silanediylbis(2-methyl-4,5-benzo-1-indenyl)ZrCl$_2$ phenyl(methyl)silanediylbis(2-methyl-α-acenaphth-1-indenyl)ZrCl$_2$ 1,2-ethanediylbis(2-methyl-4,5-benzo-1-indenyl)ZrCl$_2$ 1,2-butanediylbis(2-methyl-4,5-benzo-1-indenyl)ZrCl$_2$ dimethylsilanediylbis(2-methyl-4,5-benzo-1-indenyl)ZrCl$_2$ 1,2-butanediylbis(2-ethyl-4-phenyl-1-indenyl)ZrCl$_2$ dimethylsilanediylbis(2-ethyl-4-phenyl-1-indenyl)ZrCl$_2$ dimethylsilanediylbis(2-methyl-5-isobutyl-1-indenyl)ZrCl$_2$ phenyl(methyl)silanediylbis(2-methyl-5-isobutyl-1-indenyl)ZrCl$_2$ dimethylsilanediylbis(2-methyl-5-t-butyl-1-indenyl)ZrCl$_2$ dimethylsilanediylbis(2,5,6-trimethyl-1-indenyl)ZrCl$_2$ and the compounds listed in the examples.

The specially preferred metallocenes of formula Ia are those in which $R^1$ and $R^2$ are identical or different and are methyl or chlorine, $R^7$ is a radical

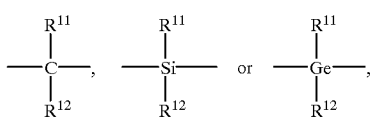

n+m is equal to zero or 1 and $R^{14}$ and $R^{15}$ are identical or different and are fluorenyl, indenyl or a substituted cyclopentadienyl. Highly preferred compounds of the formula Ia are those compounds listed in the examples.

Special importance is thus attached to (±)-phenyl(methyl) silyl-(indenyl)$_2$zirconium dichloride, diphenylmethylene(9-fluorenyl)-(cyclopentadienyl)zirconium dichloride, phenyl (methyl)methylene-(9-fluorenyl)(cyclopentadienyl) zirconium dichloride, isopropylidene(9-fluorenyl) (cyclopentadienyl)zirconium dichloride, (±)-dimethylsilyl (2,3,5-trimethyl-1-cyclopenta-dienyl)$_2$zirconium dichloride, (±)-dimethylsilyl(indenyl)$_2$zirconium dichloride, (±)-dimethylgermyl(indenyl)$_2$zirconium dichloride, (±)-dimethylsilyl(indenyl)$_2$zirconium dimethyl, (±)-phenyl (vinyl)silyl(indenyl)$_2$zirconium dichloride, (±)-phenyl (vinyl)silyl(indenyl)$_2$zirconium dimethyl,

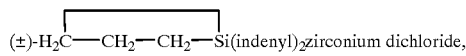
(±)-H$_2$C—CH$_2$—CH$_2$—Si(indenyl)$_2$zirconium dichloride, (±)-dimethylsilyl(2,4-dimethylcyclopentadienyl)$_2$zirconium dichloride, (±)-diphenylsilyl(2,4-dimethyl-1-cyclopentadienyl)zirconium dichloride, (±)-isopropylidene (indenyl)$_2$zirconium dichloride, (±)-dimethylsilyl(2-methyl-4,5,6,7-tetrahydro-1-indenyl)$_2$zirconium dichloride, (±)-ethylene(indenyl)$_2$zirconium dichloride, (±)-methylene(3-t-butyl-1-cyclopentadienyl)$_2$zirconium dichloride, (±)-dimethylsilyl(4,7-dimethyl-1-indenyl)$_2$zirconium dichloride, (±)-dimethylsilyl(2-methyl-1-indenyl)$_2$zirconium dichloride, (±)-phenyl(methyl)silyl(2-methyl-1-indenyl)zirconium dichloride, (±)-dimethylsilyl(2-ethyl-1-indenyl)$_2$zirconium dichloride, (±)-dimethylsilyl(4,5-benzo-1-indenyl)$_2$zirconium dichloride and (±)-dimethylsilyl(4-phenyl-1-indenyl)$_2$zirconium dichloride.

Metallocenes with C$_s$ symmetry (for example R$^{11}$R$^{12}$C (fluorenyl)-(cyclopentadienyl)zirconium dimethyl) may be used to produce a syndiotactic component in the polyolefin.

The term C$_s$ symmetry for the purposes of the present invention means that the relevant metallocenes have a plane of symmetry perpendicular to the plane occupied by Zr, R$^1$ and R$^2$. The bisector of z R$^1$—Zr—R$^2$ runs in this plane of symmetry. This consideration of symmetry is confined to a part of the zirconocene molecule, ie the bridge —(CR$^8$R$^9$)$_n$—R$^7$—(CR$^8$R$^9$)$_m$— is not taken into account. Furthermore, the term C$_s$ symmetry should be understood in a formal or idealized way. For example, shifts in the part of the molecule mentioned, which can be caused by the bridge and are open only to structural elucidation, are omitted from consideration for the purposes of the present invention.

The chiral metallocenes are used as racemic compounds for the production of highly isotactic polyolefins. However, the pure d or l form may also be used. With these pure stereoisomeric forms, an optically active polymer can be produced. The meso form of the metallocenes should however be separated off, since the polymerization-active centre (the metal atom) in these compounds is no longer chiral because of mirror-image symmetry on the central metal and can therefore not produce a highly isotactic polymer. If the meso form is not separated off, atactic polymer is obtained alongside isotactic polymer. For certain applications—flexible mouldings, for example—this can be perfectly desirable.

Separation of the stereoisomers is known in principle.

Metallocenes I and Ia may be prepared according to the following reaction principle:

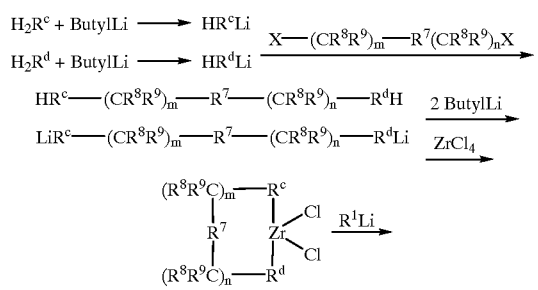

X=Cl, Br, I, O-tosyl;

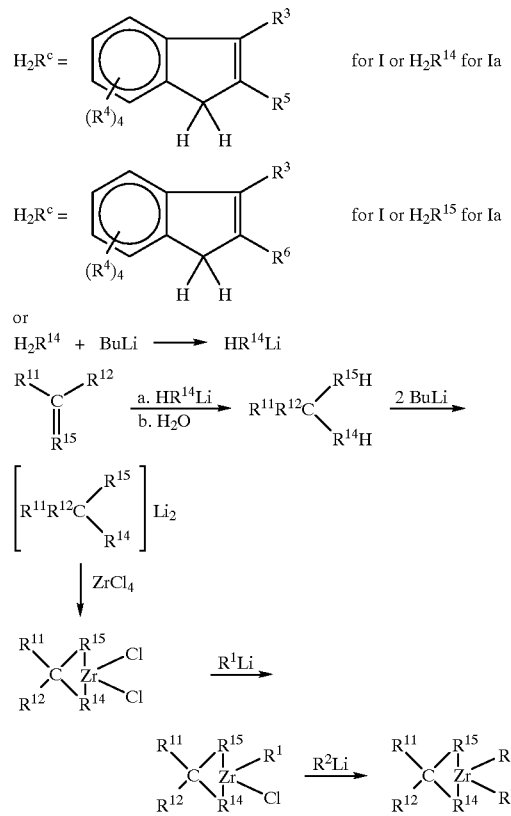

(see Journal of Organomet. chem. (1985) 63–67 and EP-A 320762).

Selection of metallocenes for the polymerization of olefins having wide or multimodal molecular weight distribution can be accomplished by carrying out a test polymerization for each metallocene.

In this process, the olefin is polymerized into a polyolefin and its average molecular weight M$_w$ and its molecular weight distribution M$_w$/M$_n$ are determined by gel permeation chromatography. Depending on the required molecular weight distribution, the metallocenes are then combined.

By including data on polymerization activity, it is possible with computer simulation of the combined gel permeation curves to obtain any required molecular weight distribution through the types of metallocenes used and their quantity ratios.

The number of zirconocenes to be used in the process according to the invention is preferably 2 or 3, in particular 2. However, a larger number of different zirconocenes (eg 4 or 5) of formulas I and Ia may also be used.

By including data on polymerization activity and molecular weight at different polymerization temperatures, in the presence of hydrogen as a molecular weight regulator or in the presence of comonomers, the computer simulation model can be further refined and the applicability of the process according to the invention further improved.

An aluminoxane of the formula II and/or III is used as the cocatalyst, with n being an integer from 0–50, preferably 10–35.

The radicals R are preferably identical and are methyl, isobutyl, phenyl or benzyl, with methyl being specially preferred.

If the radicals R are different, then they are preferably methyl and hydrogen or alternatively methyl and isobutyl, with the content of hydrogen or isobutyl being 0.01–40% (number of R radicals). Instead of the aluminoxane, a mixture consisting of aluminoxane and $AlR_3$ may be used as the cocatalyst in the polymerization, with R being as quoted above or additionally in this case R may also be ethyl.

The aluminoxane may be produced in different ways by known processes. One of the methods is, for example, to react an aluminium hydrocarbon compound and/or a hybridoaluminium hydrocarbon compound with water (gaseous, solid, liquid or bound—for example as water of crystallization) in an inert solvent (such as toluene). To produce an aluminoxane with different alkyl groups R, two different aluminium trialkyls ($AlR_3+AlR'_3$), according to the required composition, are reacted with water (see S. Pasynkiewicz, Polyhedron 9 (1990) 429 and EP-A 302 424).

The exact structure of aluminoxanes II and III is unknown (A. R. Barron et al., J. Am. Chem. Soc. 115 (1993) 4971).

Irrespective of the method of preparation, a common characteristic of all aluminoxane solutions is a changing content of unreacted aluminium parent compound which is present in free form or as an adduct.

It is possible to preactivate the metallocenes either separately or together in a mixture with an aluminoxane of the formula (II) and/or (III) before their use in the polymerization reaction. This substantially increases polymerization activity and improves grain morphology.

Preactivation of the metallocenes is carried out in solution. The metallocenes are preferably dissolved as a solid in a solution of the aluminoxane in an inert hydrocarbon. A suitable inert hydrocarbon is an aliphatic or aromatic hydrocarbon. Preferably, toluene or a $C_6$–$C_{10}$ hydrocarbon is used.

The concentration of the aluminoxane in the solution ranges from about 1% (w/w) up to the saturation limit, preferably from 5 to 30% (w/w), in each case based on the total solution. The metallocenes may be used in the same concentration but preferably they are used in an amount of $10^{-4}$–1 mol per mol aluminoxane. The preactivation time is 1 minute to 60 hours, preferably 2 to 60 minutes. The preactivation process is carried out at a temperature of $-78°$ C. to $100°$ C., preferably 0 to $70°$ C.

The metallocenes may also be prepolymerized or applied onto a carrier. For prepolymerization, preferably the (or one of the) olefin(s) used in polymerization is employed.

Suitable carriers are for example silica gels, aluminium oxides, solid aluminoxane, combinations of aluminoxane on a carrier such as silica gel, or other inorganic carrier materials. A suitable carrier material is also a polyolefin powder in finely dispersed form.

Another possible form of the process according to the invention comprises using a salt-like compound of the formula $R_xNH_{4-x}BR'_4$ or the formula $R_3PHBR'_4$ as the cocatalyst instead of or as well as an aluminoxane. In this compound, x=1, 2 or 3, R=alkyl or aryl, identical or different, and R'=aryl, which may also be fluorinated or partly fluorinated. In this case the catalyst consists of the reaction product of the metallocenes with one of the named compounds (see EP-A 277 004).

To remove catalyst poisons present in the olefin, cleaning with an aluminium alkyl, for example $AlMe_3$ or $AlEt_3$, is an advantage. This cleaning can take place in the polymerization system itself or the olefin may be brought into contact with the aluminium compound before it is added to the polymerization system and then separated off again.

The polymerization or copolymerization is carried out in the known manner in solution, in suspension or in the gas phase, continuously or batchwise, in one or more stages at a temperature of 50 to $200°$ C., preferably 50 to $100°$ C. The olefins which are polymerized or copolymerized are those of the formula $R^a$—CH=CH—$R^b$. In this formula, $R^a$ and $R^b$ are identical or different and are a hydrogen atom or an alkyl radical with 1 to 14 C atoms. $R^a$ and $R^b$ may also form a ring with the C atoms connecting them. Examples of olefins of this type are ethylene, propylene, 1-butene, 1-hexene, 4-methyl-1-pentene, 1-octene, norbornene or norbornadiene. In particular, propylene and ethylene are polymerized.

If necessary, hydrogen is added as a molecular weight regulator. The different hydrogen sensitivity of the metallocenes, and the possibility of altering the amount of hydrogen during polymerization can lead to a further desired spread of the molecular weight distribution.

The total pressure in the polymerization system is 0.5 to 100 bar. Preferably, the polymerization is carried out in the pressure range of 5 to 64 bar, which is of particular industrial relevance.

The metallocenes are used in a concentration, relative to the transition metal, of $10^{-3}$ to $10^{-8}$, preferably $10^{-4}$ to $10^{-7}$, mol of transition metal per $dm^3$ of solvent or per $dm^3$ of reactor volume. The aluminoxane or the aluminoxane/$AlR_3$ mixture is used in a concentration of $10^{-5}$ to $10^{-1}$ mol, preferably $10^{-4}$ to $10^{-2}$ mol, per $dm^3$ of solvent or per $dm^3$ of reactor volume. However, in principle, higher concentrations are also possible.

If the polymerization is carried out as suspension or solution polymerization, an inert solvent customary for the Ziegler low-pressure process is used. For example, the polymerization is carried out in an aliphatic or cycloaliphatic hydrocarbon; examples of such a hydrocarbon are butane, pentane, hexane, heptane, decane, isooctane, cyclohexane, methylcyclohexane.

Furthermore, a naphtha or hydrogenated diesel oil fraction can be used. Toluene is also usable. Preferably, the polymerization is carried out in the liquid monomer.

If inert solvents are used, the monomers are metered in as a gas or a liquid.

The duration of the polymerization is as desired, since the catalyst system to be used according to the invention shows only a small time-dependent drop in polymerization activity.

The process according to the invention is characterized by the fact that the metallocenes described exhibit very high polymerization activity in the industrially relevant temperature range between 50 and $100°$ C., producing polymers with wide, bimodal or multimodal molecular weight distribution, very high molecular weight, high stereospecificity and good grain morphology. The metallocene activity at a polymerization temperature of $50–60°$ C. is >140 kg polymer/g catalyst×hour, preferably >160 kg polymer/g catalyst×hour. At polymerization temperatures >$60°$ C., the metallocene activity is over 350, preferably over 400 kg polymer/g catalyst×hour. At polymerization temperatures of $50–60°$ C., the polymers according to the invention have a viscosity number >260, preferably >360 $cm^3$/g, at polymerization temperatures >$60°$ C., the viscosity number is over 200, preferably over 260 cm³/g. Accordingly, the molecular weight $M_w$ at polymerization temperatures above 60° C. is greater than 200 000 g/mol. $M_w/M_n$ is ≧3.0, preferably ≧4.0. $M_w/M_n$ is preferably <50, especially preferably <30.

The polymers according to the invention are particularly suitable for the production of compression moulded sheets, extruded sheets and pipes, and blow mouldings of all sizes. Preferred applications for such polymers with low flowability are, for example, blow moulded cases with integral hinges, skin packaging, sheet material for die punching, hot water tanks, wastewater and hot water pipes, pressure pipes, filter plates, heat exchangers, solid rods or automotive parts such as brake fluid reservoirs and radiator expansion tanks. In the films sector, these moulding materials are used for tear-resistant BOPP films.

The following examples are intended to illustrate the invention in more detail. The symbols have the following meanings:

VN=viscosity number in cm³/g
$M_w$=average molecular weight in g/mol determined by gel
$M_w/M_n$=molecular weight dispersity permeation chromatography
II=isotactic index (mm+½ mr) determined by $^{13}$C-NMR spectroscopy

EXAMPLES 1–12

A dry 24 dm³ reactor was flushed with propylene and filled with 12 dm³ of liquid propylene. 26 cm³ of a methylaluminoxane solution in toluene (corresponding to 35 mmol of Al, mean degree of oligomerization n=22) were then added, and the batch was stirred for 10 minutes at 30° C.

At the same time, the metallocenes provided for the polymerization were mixed (for quantities and metallocene compounds see table 1), dissolved in 10 m³ of methylaluminoxane solution in toluene (13 mmol Al) and after 2 minutes poured into the reactor.

Polymerization was carried out for 1 hour at the polymerization temperature quoted in table 1 and then the polymerization reaction was stopped with 12 Ndm³ of $CO_2$ gas. The polymer was dried for 24 hours at 80° C. in vacuo.

The results of the polymerization are shown in table 1, in which Me=methyl.

TABLE 1

| Metallocene mixture | Polym. temp. (° C.) | Yield (kg) | Activity [kgPP/gcatxh] | VN (cm³/g) | $M_w$ (g/mol) | $M_w/M_n$ | II (%) | Ex. |
|---|---|---|---|---|---|---|---|---|
| 1.5 mg (±)-Me₂Si(2-methyl-4-phenyl-1-indenyl)₂ZrCl₂<br>3.0 mg (±)-Me₂Si(indenyl)2-ZrCl₂ | 50 | 1.95 | 433.0 | 568 | 704 000 | 15.7 bimodal | 98.9 | 1 |
| 1.1 mg (±)-Me₂Si(2-methyl-4-(1-naphthyl)-1-indenyl)₂ZrCl₂<br>11.5 mg Ph₂C(fluorenyl)-(cyclopentadienyl)ZrCl₂ | 60 | 1.80 | 142.8 | 560 | 764 000 | 6.9 | — | 2 |
| 0.5 mg (±)-Me₂Si(2-methyl-4-(1-naphthyl)-1-indenyl)₂ZrCl₂<br>5.0 mg Me₂C(fluorenyl)(cyclopentadienyl)ZrCl₂ | 70 | 1.96 | 356.4 | 315 | 435 000 | 4.5 | — | 3 |
| 5.0 mg (±)-Me₂Si(2-methyl-4,6-diisopropyl-1-indenyl)₂-ZrCl₂<br>5.0 mg (f)-Me₂Ge(indenyl)₂-ZrCl₂ | 50 | 1.98 | 198.5 | 265 | 332 000 | 8.4 | 97.3 | 4 |
| 4.3 mg (±)-Ph(Me)Si(2,4,6-trimethyl-1-indenyl)₂ZrCl₂<br>4.7 mg (±)-Me₂C(indenyl)₂-ZrCl₂ | 50 | 1.44 | 160.0 | 260 | 265 500 | 14.5 bimodal | 89.5 | 5 |
| 1.7 mg (±)-Me₂Si(2-methyl-4-isopropyl-1-indenyl)₂ZrCl₂<br>8.8 mg (±)-Me₂Si(2,3,5-trimethyl-1-cyclopentadienyl)₂-ZrCl₂ | 50 | 1.78 | 169.5 | 265 | 305 000 | 9.4 bimodal | 98.4 | 6 |
| 1.8 mg (±)-Me₂Si(2-methyl-4,5-benzo-1-indenyl)₂ZrCl₂<br>9.5 mg (±)-Me₂Si(2-methyl-4,5,6,7-tetrahydro-1-indenyl)₂-ZrCl₂ | 70 | 2.35 | 208.0 | 205 | 288 000 | 10.5 bimodal | 96.7 | 7 |
| 1.0 mg (±)-Ph(Me)Si(2-methyl-α-acenaphth-1-indenyl)₂ZrMe₂<br>4.0 mg (±)-Ph(vinyl)Si-(indenyl)₂ZrMe₂ | 70 | 1.92 | 384.0 | 207 | 205 500 | 8.4 bimodal | 97.3 | 8 |
| 2.5 mg (±)-Me₂Si(2,5,6-trimethyl-1-indenyl)₂ZrCl₂<br>1.5 mg (±)-Ph₂Si(2,4-dimethyl-1-cyclopentadienyl)₂-ZrCl₂ | 55 | 1.02 | 255.0 | 276 | 289 500 | 6.4 | 96.4 | 9 |
| 2.5 mg (±)-Me₂Si(2-methyl-4,5-benzo-1-indenyl)₂ZrCl₂<br>1.5 mg (±)-Me₂Si(4,5-benzo-1-indenyl)₂ZrCl₂ | 70 | 1.95 | 488.0 | 203 | 265 000 | 10.5 bimodal | 97.9 | 10 |
| 0.7 mg (±)-Me₂Si(2-methyl-4-phenyl-1-indenyl)₂ZrCl₂ | 70 | 1.70 | 362.0 | 298 | 403 500 | 17.4 bimodal | 98.0 | 11 |

TABLE 1-continued

| Metallocene mixture | Polym. temp. (° C.) | Yield (kg) | Activity [kgPP/gcatxh] | VN (cm³/g) | $M_w$ (g/mol) | $M_w/M_n$ | II (%) | Ex. |
|---|---|---|---|---|---|---|---|---|
| 4.0 mg (±)-Me₂Si(4-phenyl-1-indenyl)₂ZrCl₂ 0.5 mg (±)-Me₂Si(2-methyl-4-(1-naphthyl)-1-indenyl)₂ZrCl₂ 5.0 mg (±)-Me₂Si(2,4,6-trimethyl-1-indenyl)₂ZrCl₂ | 70 | 2.07 | 376.5 | 345 | 496 000 | 8.5 | 96.8 | 12 |
| 0.5 mg (±)-Me₂Si(2-methyl-4-phenyl-1-indenyl)₂ZrCl₂ 4.4 mg (±)-Me₂Si(2,4,6-trimethyl-1-indenyl)₂ZrCl₂ 0.8 mg (±)-ethylidene (indenyl)₂ZrCl₂ | 70 | 2.33 | 408.8 | 261 | 349 500 | 14.0 multimodal | 95.0 | 13 |

EXAMPLE 14

Example 1 was repeated but, before addition of the propylene, 3 Ndm³ of hydrogen gas were introduced into the reactor.

2.85 kg of polymer were obtained and the metallocene activity was thus 633.3 kg PP/g catxh.

VN=319 cm³/g; $M_w$=369 000 g/mol, $M_w/M_n$=12.0

The distribution was bimodal, II=99.1%.

EXAMPLE 15

Example 1 was repeated but in addition 100 g of ethylene were metered in continuously during the polymerization.

2.24 kg of copolymer were obtained and the metallocene activity was thus 497.8 kg copolymer/g catxh.

VN=269 cm³/g; $M_w$=305 000 g/mol, $M_w/M_n$=9.2.

4.2% (w/w) of ethylene was determined in the polymer by infrared spectroscopy.

EXAMPLE 16

Example 15 was repeated but 250 g of ethylene were added in one portion and this only after 30 minutes.

2.05 kg of block copolymer were obtained and the metallocene activity was thus 455.6 kg copolymer/g catxh.

VN=279 cm³/g; $M_w$=268 000 g/mol, $M_w/M_n$=7.2.

The ethylene content as determined by infrared spectroscopy was 12.1% (w/w).

What is claimed is:

1. A process for the preparation of a polyolefin having a molecular weight distribution $M_w/M_n \geq 3.0$, which may be monomodal, bimodal or multimodal, by polymerization or copolymerization of an olefin of the formula $R^a CH=CHR^b$, in which $R^a$ and $R^b$ are identical or different and are a hydrogen atom or an alkyl radical with 1 to 14 carbon atoms, or $R^a$ and $R^b$ may from a ring system together with the atoms connecting them, at a temperature of 50–200° C., at a pressure of 0.5 to 100 bar, in solution, in suspension or in a gas phase, in the presence of a catalyst which consists essentially of a transition metal component (metallocene) and an aluminoxane of the formula

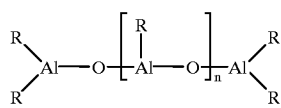

(II)

for the linear type and/or formula III

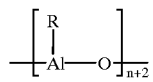

(III)

for the cyclic type, in which the radicals R in the formulae II and III may be identical or different and are a $C_1$–$C_6$ alkyl group, a $C_1$–$C_6$ fluoroalkyl group, $C_6$–$C_{18}$ aryl group, fluoroaryl group, or hydrogen and n is an integer from 0 to 50, or, of the aluminoxane, a mixture of an aluminoxane of the formula II and/or the formula III with an $AlR_3$ compound, wherein at least two different zirconocenes with at least one zirconocene of the formula I and at least one zirconocene of the formula Ia are used as the transition component,

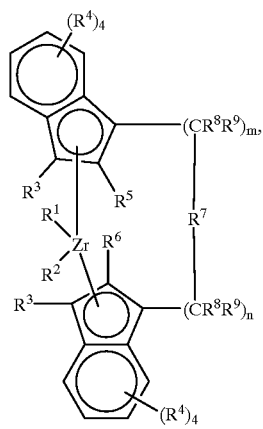

(I)

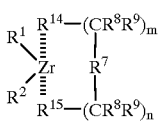

(Ia)

in which $R^1$ and $R^2$ are identical or different and are a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_7$–$C_{40}$ arylalkyl group, a $C_7$–$C_{40}$ alkylaryl group, a $C_8$–$C_{40}$ arylalkenyl group or a halogen atom, R³ is a hydrogen atom, a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, R⁴ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, where at least one R⁴ radicals per indenyl ring is different from hydrogen, or two or more R⁴ radicals form a ring system with the atoms connecting them, R⁵ and R⁶ are identical or different and are a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, R⁷ is

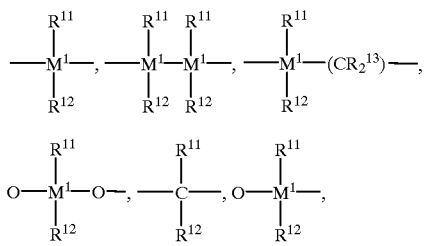

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or $R^{11}$ and $R^{12}$ or $R^{11}$ and $R^{13}$ each form a ring with the atoms connecting them, M¹ is silicon, germanium or tin, R⁸ and R⁹ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or R⁸ and R⁹ each form a ring with the atoms connecting them, $R^{14}$ and $R^{15}$ are identical or different and are monocyclic or polycyclic hydrocarbon radical which may form a sandwich structure with the zirconium atom and m and n are identical or different and are zero, 1 or 2, with m plus n being equal to zero, 1 or 2.

2. A process for the preparation of a polyolefin having a molecularweight distribution $M_w/M_n \geq 3.0$, which may be monomodal, bimodal or multimodal, by polymerization or copolymerization of an olefin of the formula $R^a CH = CHR^b$, in which $R^a$ and $R^b$ are identical or different and are a hydrogen atom or an alkyl radical with 1 to 14 carbon atoms, or $R^a$ and $R^b$ may from a ring system together with the atoms connecting them, at a temperature of 50–200 °C., at a pressure of 0.5 to 100 bar, in solution, in suspension or in a gas phase, in the presence of a catalyst which consists essentially of a transition metal component (metallocene) and an aluminoxane of the formula

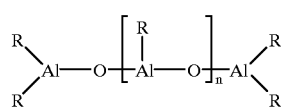

(II)

for the linear type and/or formula III

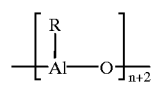

(III)

for the cyclic type, in which the radicals R in the formulae II and III may be identical or different and are a $C_1$–$C_6$ alkyl group, a $C_1$–$C_6$ fluoroalkyl group, $C_6$–$C_{18}$, aryl group, fluororyl group, or hydrogen and n is an integer from 0 to 50, or, of the aluminoxane, a mixture of an aluminoxane of the formula II and/or the formula III with an $AlR_3$ compound, wherein at least two different zirconocenes of the formula I are used as the transition component,

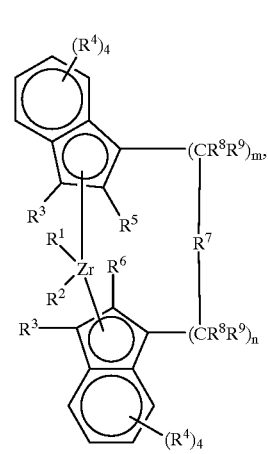

(I)

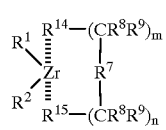

(Ia)

in which

R¹ and R² are identical or different and are a hydrogen atom, a $C_1$–$C_{10}$ alkyl group, a $C_1$–$C_{10}$ alkoxy group, a $C_6$–$C_{10}$ aryl group, a $C_6$–$C_{10}$ aryloxy group, a $C_2$–$C_{10}$ alkenyl group, a $C_7$–$C_{40}$ arylalkyl group, a $C_7$–$C_{40}$ alkylaryl group, a $C_8$–$C_{40}$ arylalkenyl group or a halogen atom, R³ is a hydrogen atom, a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, $R^4$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, where at least one $R^4$ radicals per indenyl ring is different from hydrogen, or two or more $R^4$ radicals form a ring system with the atoms connecting them, $R^5$ and $R^6$ are identical or different and are a halogen atom, a $C_1$–$C_{10}$ alkyl group, which may be halogenated, a $C_6$–$C_{10}$ aryl group, a $C_2$–$C_{10}$ alkenyl group, a $C_7$–$C_{40}$ arylalkyl group, a $C_7$–$C_{40}$ alkyloxy group, a $C_8$–$C_{40}$ arylalkenyl group, an —$NR_2^{10}$, —$OR^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$ alkyl group or a $C_6$–$C_{10}$ aryl group, $R^7$ is

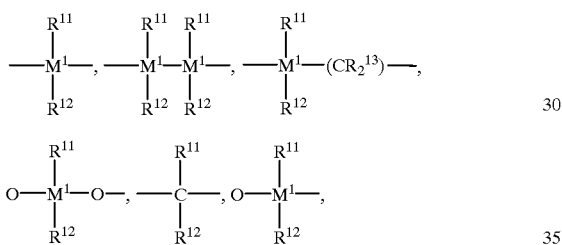

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or $R^{11}$ and $R^{12}$ or $R^{11}$ and $R^{13}$ each form a ring with the atoms connecting them, $M^1$ is silicon, germanium or tin, $R^8$ and $R^9$ are identical or different and are a hydrogen atom, a halogen atom, a $C_1$–$C_{20}$ alkyl group, a $C_1$–$C_{20}$ fluoroalkyl group, a $C_6$–$C_{30}$ aryl group, a $C_6$–$C_{30}$ fluoroaryl group, a $C_1$–$C_{20}$ alkoxy group, a $C_2$–$C_{20}$ alkenyl group, a $C_7$–$C_{40}$ arylalkyl group, a $C_8$–$C_{40}$ arylalkenyl group, a $C_7$–$C_{40}$ alkylaryl group, or $R^8$ and $R^9$ each form a ring with the atoms connecting them, m and n are identical or different and are zero, 1 or 2, with m plus n being equal to zero, 1 or 2.

3. The process as claimed in claim 2, wherein $R^1$ and $R^2$ are identical or different and are methyl or chlorine, $R^3$ is hydrogen and $R^7$ is a radical

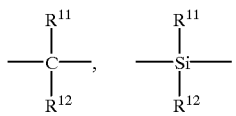

with n plus m being equal to zero or 1.

4. The process as claimed in claim 2, wherein the metallocene of formula I is selected from the group consisting of dimethylsilanediylbis(2-methyl-4-phenyl-1-indenyl)ZrCl$_2$, phenyl(methyl)silanediylbis(2-methyl-4-phenyl-1-indenyl)ZrCl$_2$, dimethylsilanediylbis(2-methyl-4-(1-naphthyl)-1-indenyl)ZrCl$_2$, dimethylsilanediylbis(2-methyl-4-(2-naphthyl)-1-indenyl)ZrCl$_2$, dimethylsilanediylbis(2-ethyl-4-(1-naphthyl)-1-indenyl)ZrCl$_2$, dimethylsilanediylbis(2-methyl-4,6-diisopropyl-1-indenyl)ZrCl$_2$, dimethylsilanediylbis(2,4,6-trimethyl-1-indenyl)ZrCl$_2$, phenyl(methyl)silanediylbis(2-methyl-4,6-diisopropyl-1-indenyl)ZrCl$_2$, phenyl(methyl)silanediylbis(2,4,6-trimethyl-1-indenyl)ZrCl$_2$, 1,2-ethanediylbis(2-methyl-4,6-diisopropyl-1-indenyl)ZrCl$_2$, 1,2-butanediylbis(2-methyl-4,6-diisopropyl-1-indenyl)ZrCl$_2$, dimethylsilanediylbis(2-methyl-4-ethyl-1-indenyl)ZrCl$_2$, dimethylsilanediylbis(2-methyl-4-isopropyl-1-indenyl)ZrCl$_2$, dimethylsilanediylbis(2-methyl-4-t-butyl-1-indenyl)ZrCl$_2$, phenyl(methyl)silanediylbis(2-methyl-4-isopropyl-1-indenyl)ZrCl$_2$, dimethylsilanediylbis(2-ethyl-4-methyl-1-indenyl)ZrCl$_2$, dimethylsilanediylbis(2,4-dimethyl-1-indenyl)ZrCl$_2$, dimethylsilanediylbis(2-methyl-4-ethyl-1-indenyl)ZrCl$_2$, dimethylsilanediylbis(2-methyl-α-acenaphth-1-indenyl)ZrCl$_2$, phenyl(methyl)silanediylbis(2-methyl-4,5-benzo-1-indenyl)ZrCl$_2$, phenyl(methyl)silanediylbis(2-methyl-α-acenaphth-1-indenyl)ZrCl$_2$, 1,2-ethanediylbis(2-methyl-4,5-benzo-1-indenyl)ZrCl$_2$, 1,2-butanediylbis(2-methyl-4,5-benzo-1-indenyl)ZrCl$_2$, dimethylsilanediylbis(2-methyl-4,5-benzo-1-indenyl)ZrCl$_2$, 1,2-butanediylbis(2-ethyl-4-phenyl-1-indenyl)ZrCl$_2$, dimethylsilanediylbis(2-ethyl-4-phenyl-1-indenyl)ZrCl$_2$, dimethylsilanediylbis(2-methyl-5-isobutyl-1-indenyl)ZrCl$_2$, phenyl(methyl)silanediylbis(2-methyl-5-isobutyl-1-indenyl)ZrCl$_2$, dimethylsilanediylbis(2-methyl-5-t-butyl-1-indenyl)ZrCl$_2$ and dimethylsilanediylbis(2,5,6-trimethyl-1-indenyl)ZrCl$_2$.

5. The process as claimed in claim 2, wherein propylene is polymerized or propylene and ethylene are copolymerized.

6. The process as claimed in claim 3, wherein propylene is polymerized or propylene and ethylene are copolymerized.

7. The process as claimed in claim 4, wherein propylene is polymerized or propylene and ethylene are copolymerized.

8. The process as claimed in claim 3, wherein $R^1$ and $R^2$ are chlorine, $R^{11}$ and $R^{12}$ are identical or different and are phenyl or methyl and n plus m being equal to zero.

9. The process as claimed in claim 6, wherein $R^1$ and $R^2$ are chlorine, $R^{11}$ and $R^{12}$ are identical or different and are phenyl or methyl and n plus m being equal to zero.

10. The process as claimed in claim 1, wherein said catalyst is a supported catalyst.

11. The process as claimed in claim 2, wherein said catalyst is a supported catalyst.

12. The process as claimed in claim 10, wherein said support is silica gel, aluminum oxide, solid aluminoxane or combinations thereof.

13. The process as claimed in claim 11, wherein said support is silica gel, aluminum oxide, solid aluminoxane or combinations thereof.

* * * * *

UNITED STATES PATENT AND TRADEMARK OFFICE
CERTIFICATE OF CORRECTION

PATENT NO.   : 6,150,481
DATED        : November 21, 2000
INVENTOR(S)  : Andreas Winter et al.

It is certified that error appears in the above-identified patent and that said Letters Patent is hereby corrected as shown below:

Column 13,
Line 54, "from" should read -- form --.

Column 16,
Line 2, "from" should read -- form --; and
Line 50, delete the formula (Ia).

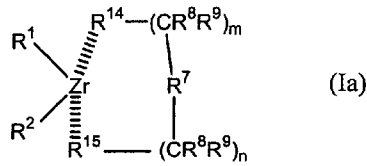

(Ia)

Signed and Sealed this

Twenty-seventh Day of August, 2002

Attest:

JAMES E. ROGAN
Attesting Officer   Director of the United States Patent and Trademark Office